US007986823B2

(12) United States Patent
Wang et al.

(10) Patent No.: US 7,986,823 B2
(45) Date of Patent: Jul. 26, 2011

(54) SYSTEM AND METHOD FOR CONSISTENT DETECTION OF MID-SAGITTAL PLANES FOR MAGNETIC RESONANCE BRAIN SCANS

(75) Inventors: Yiwen Wang, Gainesville, FL (US); Li Zhang, Skillman, NJ (US)

(73) Assignee: Siemens Aktiengesellschaft, Munich (DE)

( * ) Notice: Subject to any disclaimer, the term of this patent is extended or adjusted under 35 U.S.C. 154(b) by 749 days.

(21) Appl. No.: 12/116,461

(22) Filed: May 7, 2008

(65) Prior Publication Data

US 2008/0285829 A1 Nov. 20, 2008

Related U.S. Application Data

(60) Provisional application No. 60/917,768, filed on May 14, 2007.

(51) Int. Cl.
*G06K 9/00* (2006.01)
(52) U.S. Cl. ............................................ 382/131; 378/4

(58) Field of Classification Search .............. 378/4, 901; 600/425, 410; 382/131
See application file for complete search history.

(56) References Cited

U.S. PATENT DOCUMENTS

2007/0276219 A1* 11/2007 K.N. et al. .................... 600/410
* cited by examiner

*Primary Examiner* — Hoon Song

(57) ABSTRACT

A method for finding consistent mid-sagittal planes (MSPs) in a pair of 3D image head scans of a same patient includes, for each image, selecting a 2D transverse localizer image from a middle slice along a transverse view of the 3D image, fitting an ellipse to the transverse localizer image to locate a head position (x, y), where the y-coordinate is indicative of a position of a 2D coronal localizer image in the 3D image, fitting an ellipse to the coronal localizer image to locate a head position (x, y) in the coronal localizer image, calculating a middle line in the transverse localizer image and a middle line in the coronal localizer image, calculating an MSP from the middle lines, and determining a new set of slope and intercept parameters for one MSP that maximizes a similarity measure between the one MSP and the other MSP.

21 Claims, 16 Drawing Sheets

------ Sym Line: k=91.7184 degree, c=250

(a)

------ Sym Line: k=88.4061 degree, c=268.7188
—— Consist tune: k=88.3373 degree, c=272.9153

(b)

------ Sym Line: k=91.7184 degree, c=250

(a)

------ Sym Line: k=88.4061 degree, c=268.7188
—— Consist tune: k=91.1175 degree, c=260.9167

(b)

definition of object of interest

SYSTEM AND METHOD FOR CONSISTENT DETECTION OF MID-SAGITTAL PLANES FOR MAGNETIC RESONANCE BRAIN SCANS

CROSS REFERENCE TO RELATED UNITED STATES APPLICATIONS

This application claims priority from "Consistent Detection of Mid-Sagittal Planes for Follow-up MR Brain Studies", U.S. Provisional Application No. 60/917,768 of Wang, et al, filed May 14, 2007, the contents of which are herein incorporated by reference in their entirety.

TECHNICAL FIELD

This disclosure is directed to the detection of mid-sagittal planes in magnetic resonance (MR) images.

DISCUSSION OF THE RELATED ART

In current MRI clinical brain examinations, the mid-sagittal planes (MSP) are important anatomic landmarks for standardizing the visualization of important anatomy for further scan planning. The accuracy and the consistency of the geometry of the diagnostic scan are both required. The accuracy describes the difference between the automatic detection by computer-based algorithm and the diagnostic scan prescribed by MRI operators for the same image. The smaller is the difference, the more accurate is the algorithm. The consistency refers to the stationary geometry detection of MSP for images acquired at the different time points. For the automatic detection of the MSP, even if results from a computer-based algorithm has a geometric error as compared to the operator's golden standard in a first study, consistency will compensate in a second study and use the same scan plane for a comparable study.

SUMMARY OF THE INVENTION

Exemplary embodiments of the invention as described herein generally include methods and systems for automatically detecting consistent MSPs for 2 different scans of a same patient. An algorithm according to an embodiment of the invention includes: (1) preprocessing a 3D localizer to select the coronal and transverse view to build the initial MSP for both scans; and (2) assigning one study as a reference study, the other as a composed study, and implementing an optimization algorithm to tune the parameters of the midline (k, c) to adapt the sagittal plane of the composed study according to the similarity measure to the MSP of the reference study.

According to an aspect of the invention, there is provided a method for finding consistent mid-sagittal planes (MSPs) in different image head scans of a same patient, the method including providing a pair of images acquired from different head scans of a same patient, each said image comprising a plurality of intensities associated with a 3-dimensional (3D) grid of points, for each image, selecting a 2-dimensional (2D) transverse localizer image from a middle slice along a transverse view of the 3D image, fitting an ellipse to said transverse localizer image to locate a head position (x, y) in said transverse localizer image, wherein said y-coordinate, a position along a vertical axis, is indicative of a position of a 2D coronal localizer image in the 3D image, fitting an ellipse to said coronal localizer image to locate a head position (x, y) in said coronal localizer image, wherein said x-coordinate, a position along a horizontal axis, is indicative of a position of said 2D coronal localizer image in the 3D image, calculating a middle line in said transverse localizer image and a middle line in said coronal localizer image, calculating a mid-sagittal plane (MSP) from the middle lines of said transverse localizer image and said coronal localizer image, and determining a new set of slope and intercept parameters within a proximity of one MSP that maximizes a similarity measure between the one new MSP and the other MSP.

According to a further aspect of the invention, if the middle lines of said transverse localizer image and said coronal localizer image intersect each other, calculating said mid-sagittal plane from the plane defined by the intersection of said middle lines.

According to a further aspect of the invention, if the middle lines of said transverse localizer image and said coronal localizer image do not intersect each other, calculating said mid-sagittal plane further comprises finding points $p_1$, $p_2$ on each respective middle lines that are closest to each other, finding a mid-pint $p_m$ on a line segment connecting points $p_1$, $p_2$, and defining said MSP as a plane passing through point $p_m$ that whose normal is determined by a cross product of vectors corresponding to said middle lines.

According to a further aspect of the invention, the method includes, for each 3D image, updating a column resolution and row resolution of said corresponding MSP with information from each selected transverse and coronal localizer image.

According to a further aspect of the invention, the slope and intercept parameters are the slope and intercept of the middle lines of the transverse localizer image and the coronal localizer image associated with the MSP.

According to a further aspect of the invention, the similarity measure is a mutual information measure proportional to $$-\sum_x \sum_y p(x, y) \log\left(\frac{p(x, y)}{p(x)p(y)}\right),$$

wherein x, y represent respectively intensity levels of corresponding points in each of the two MSPs, p(x) is a probability of intensity level x, and p(x, y) is a joint probability of intensity levels x, y.

According to a further aspect of the invention, the similarity measure is maximized using a simplex algorithm.

According to a further aspect of the invention, the method includes generating a new sagittal plane for the one 3D image from said new set of slope and intercept parameters, re-interpolating said new sagittal plane into a same resolution as the MSP of the other 3D image, matching the re-interpolated sagittal plane and the other MSP at a center of mass point of each sagittal image, defining an object of interest as an overlap area of the two sagittal images with the center of mass points registered, and calculating said similarity measure over said object of interest.

According to a further aspect of the invention, the method includes repeating the steps of claim 20 until said similarity measure converges to a maximum value.

According to another aspect of the invention, there is provided a program storage device readable by a computer, tangibly embodying a program of instructions executable by the computer to perform the method steps for finding consistent mid-sagittal planes (MSPs) in different image head scans of a same patient.

DETAILED DESCRIPTION OF EXEMPLARY EMBODIMENTS

Figure 1:
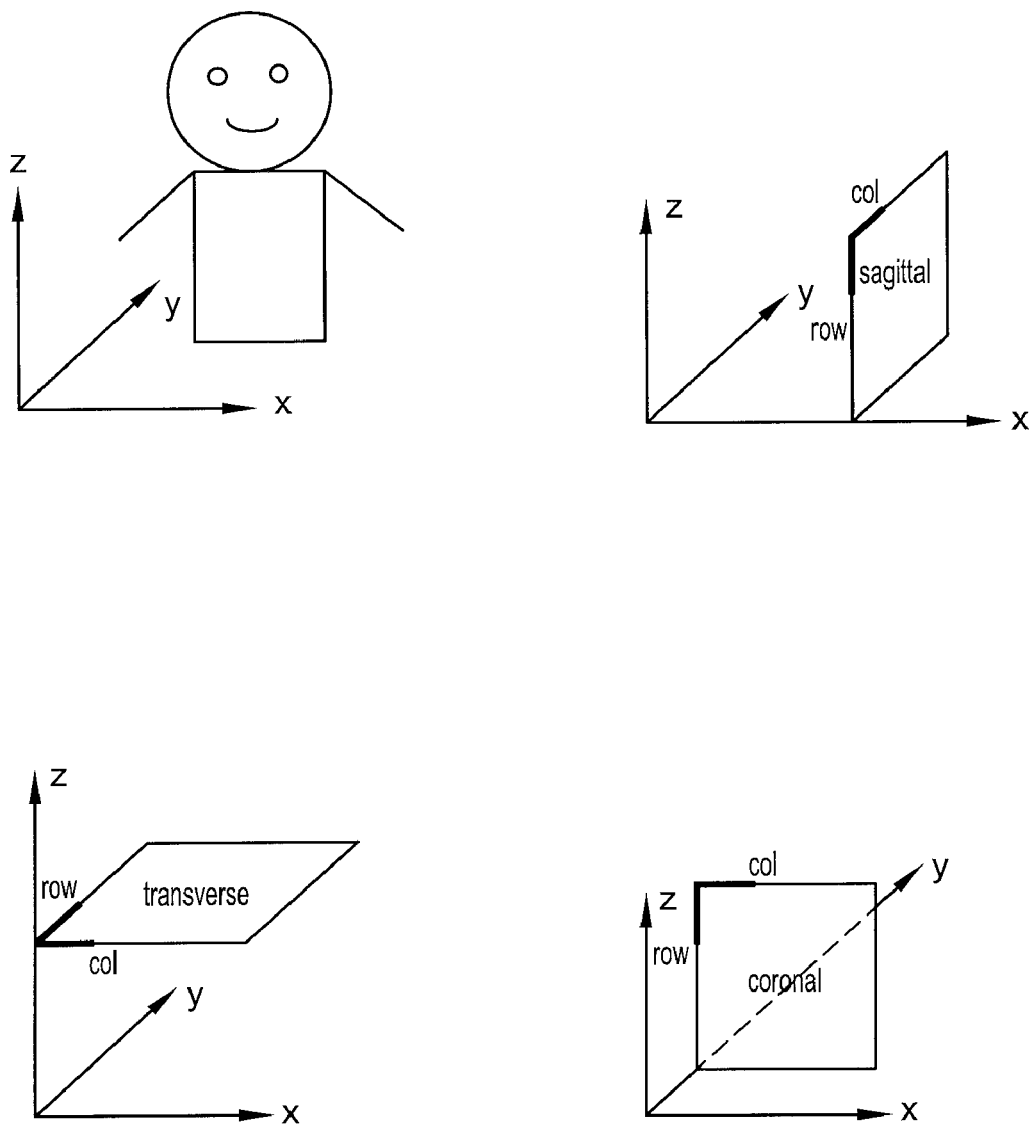
FIG. 1 depicts a 3D coordinate system definition, according to an embodiment of the invention.

Exemplary embodiments of the invention as described herein generally include systems and methods for detection of mid-sagittal planes in magnetic resonance (MR) images. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Coordinate System and Notations

An exemplary, non-limiting coordinate system according to an embodiment of the invention is the DICOM coordinate system. In this coordinate system, the 3D x axis points from the right side to the left side, the 3D y axis points from front to the back, and the 3D z axis points from feet to the head.

A method according to an embodiment of the invention starts with a 3D localizer image of a patient's head with isotropic resolution. In one exemplary, non-limiting embodiment, the resolution is [1.4, 1.4, 1.4] mm. Using the DICOM coordinate system, the column vector of transverse localizer is 3D x axis, and the row vector is 3D y axis. The column vector of coronal localizer is 3D x axis, and the row vector is 3D-z axis. The column vector of the sagittal localizer is 3D y axis, and the row vector is 3D-z axis. The normal direction, along which the slice number increases, is calculated as cross product of column vector and row vector: $\overrightarrow{norm} = \overrightarrow{col} \times \overrightarrow{row}$.

FIG. 1 depicts a typical DICOM 3D coordinate system definition with respect to a schematic of a patient's body and head, including the sagittal, transverse, and coronal views, according to an embodiment of the invention.

Computing the Initial Sagittal Plane

An initial MSP is computed from 2D coronal and transverse localizer images selected from the 3D localizer. While the MSP is calculated in a 2D coordinate system, the column vector for each localizer view is 2D horizontal axis, and the row vector is 2D vertical axis.

Figure 2:
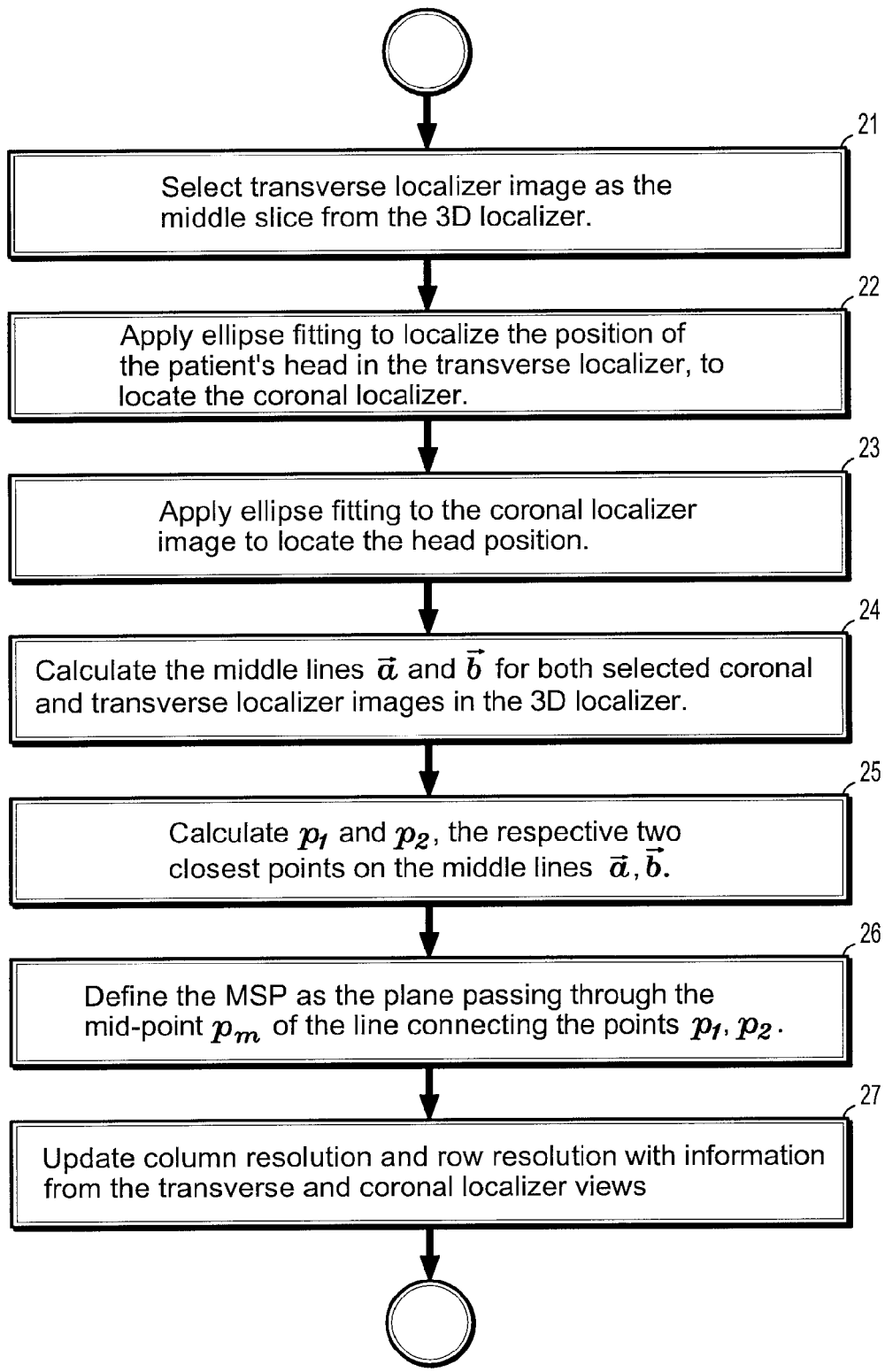
FIG. 2 is a flowchart of an exemplary method for selecting transverse and coronal localizer views for computing the sagittal plane, according to an embodiment of the invention.
Figure 3:
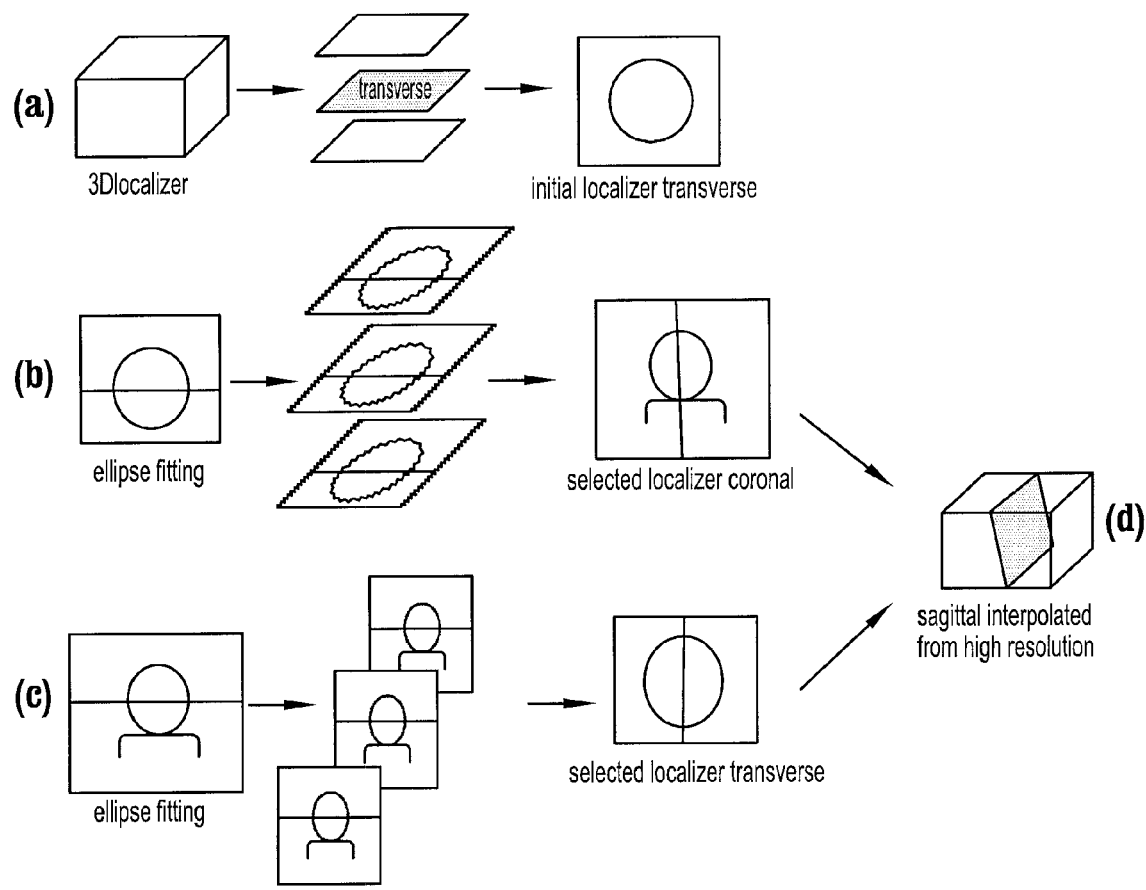
FIGS. 3(a)-(d) illustrate an exemplary method for selecting transverse and coronal localizer views for computing the sagittal plane, according to an embodiment of the invention.

FIG. 2 is a flowchart of an exemplary method for selecting transverse and coronal localizer views for computing the sagittal plane, and FIGS. 3(a)-(d) illustrate the method according to an embodiment of the invention. Referring to FIG. 2, an exemplary initial transverse localizer image is selected at step 21 as the middle slice from the 3D localizer transverse view, shown in FIG. 3(a). Then, at step 22, an ellipse fitting is applied to localize the position of the patient's head (cx, cy), where cx indicates the position along the horizontal (column) direction in the transverse view, and cy indicates the position along the vertical (row) direction in the transverse view, and yields the slice position of the coronal localizer view in the 3D localizer, as shown in FIG. 3(b). At step 23, the ellipse fitting is applied again to the coronal localizer image to locate the head position, shown in FIG. 3(c), where cy, the position along the vertical direction, yields the refined slice position of the transverse view in the 3D localizer. Then the selected transverse and coronal localizer images, respectively calculated by cy from coronal and transverse ellipse fitting, are used to generate the initial MSP, as shown in FIG. 3(d) and described in the next paragraph.

Figure 4:
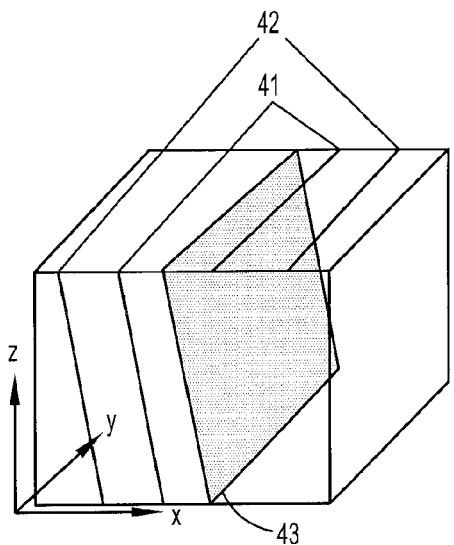
FIG. 4 shows a non-unique MSP by parallel middle line groups, according to an embodiment of the invention.

The middle lines for both selected coronal and transverse localizer images, denoted $\vec{a}$ and $\vec{b}$, respectively, are calculated in the 3D localizer image at step 24. In the 3D coordinate system, these two lines might not intersect each other but might be spaced apart from each other. If the lines do intersect each other, then the plane defined by the two middle lines can be taken as the MSP. If the two middle lines do not intersect, then calculate $p_1$ and $p_2$, the respective two closest points on the middle lines $\vec{a}$ and $\vec{b}$, at step 25. The MSP can then be defined at step 26 as the plane passing through the mid-point $p_m$ of $p_1$ and $p_2$ and normal to the line connecting $p_1$ and $p_2$. In this way, if there is a group of the parallel middle lines having a same 2D slope $k_1$ but different 2D intercept $c_1$ for the coronal localizer view, and a same 2D slope $k_2$ but a different 2D intercept $c_2$ for the transverse localizer view, when the coronal and transverse middle lines have the same intercepts sum $c_1+c_2$ on the x axis, the mid-point $p_m$ ends up the same. The idea is illustrated in FIG. 4, where a first group 41 of middle lines and a second group 42 of middle lines end up having the same MSP 43. The geometry of MSP is then defined by the normal direction $\vec{n}$ passing through point $p_m$, where the normal direction is calculated by $\vec{n}=\vec{a}\times\vec{b}$. The column resolution and row resolution are updated at step 27 with the corresponding information from the selected transverse and coronal localizer views. Steps 21 to 27 are applied for both scan 1 and scan 2. Optionally, according to other embodiments of the invention, based on the geometry of the MSP, a group of parallel sagittal images having the same image width and heights is resampled from the 3D localizer for both scans.

Consistency Tuning of the Sagittal Plane to the Reference Image

Consistency is achieved between the two scans from the same patient by maximizing a similarity between two corresponding images. The idea of consistency tuning is to find a sagittal plane in the composed study similar to one in the reference study. Based on the initial MSP calculated by the steps of FIG. 2, four parameters ($k_1$, $c_1$, $k_2$, $c_2$) are calculated by an optimization algorithm to maximize a similarity measure (or minimize the negative value of the similarity measure) between the interpolated sagittal image, generated by $k_1$, $c_1$, $k_2$, $c_2$, and the reference image. An exemplary, non-limiting optimization method is the simplex algorithm. There are two issues of concern: (1) selection of a proper similarity measure; and (2) validation of the consistency tuning.

There are several possible similarity measures between two images. A cost function to be minimized can be defined using the following non-limiting list of similarity measures.

Correlation Coefficient (CC):

$$E = -\left|\frac{\frac{\sum_i(x_i-\bar{x})(y_i-\bar{y})}{N}}{\sqrt{\frac{\sum_i(x_i-\bar{x})(x_i-\bar{x})}{N}\frac{\sum_i(y_i-\bar{y})(y_i-\bar{y})}{N}}}\right|.$$

Mean Square Error (MSE):

$$E = \frac{\sum_i(x_i-y_i)^2}{N}.$$

Kullback-Leibler's Divergence (KLD):

$$E = \sum_x p(x)\log\frac{p(x)}{q(y)}.$$

Mutual Information (MI):

$$E = -\sum_x\sum_y p(x,y)\log\left(\frac{p(x,y)}{p(x)p(y)}\right).$$

Normalized Mutual Information (NMI):

$$E = \frac{H(x,y)}{H(x)+H(y)}, \text{ where } H(x) = -\sum_x p(x)\log p(x).$$

Figure 5:
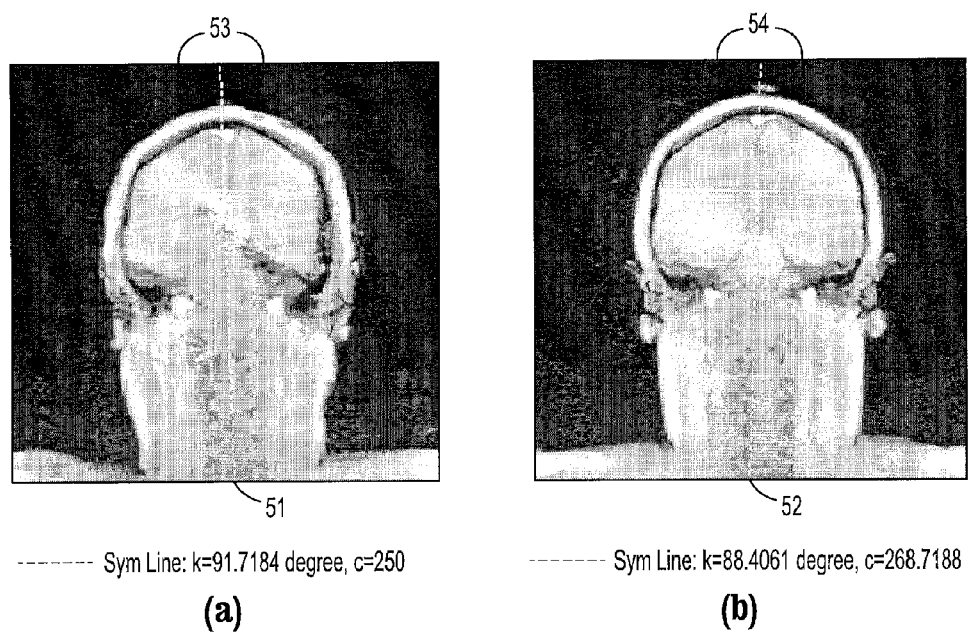
FIGS. 5(a)-(b) show initial middle lines for a reference study and a composed study, according to an embodiment of the invention.

For each of these similarity measures, x, y represent respectively the gray levels of corresponding points in each of the two MSP images, p(x) is a probability of gray level x, and p(x, y) is the joint probability of gray levels x, y. All of the above criteria have been studied for 2D image consistency tuning for the same patient. These similarity measures are calculated using image information along the middle line within a tuning range in the reference study to consistently tune the middle line in the composed study. FIG. 5(a)-(b) show initial middle lines 51, 52 within tuning ranges 53, 54 for a reference study (FIG. 5(a)) and a composed study (FIG. 5(b)), with the slopes and intercepts as indicated in the caption below each figure, according to an embodiment of the invention.

Figure 6:
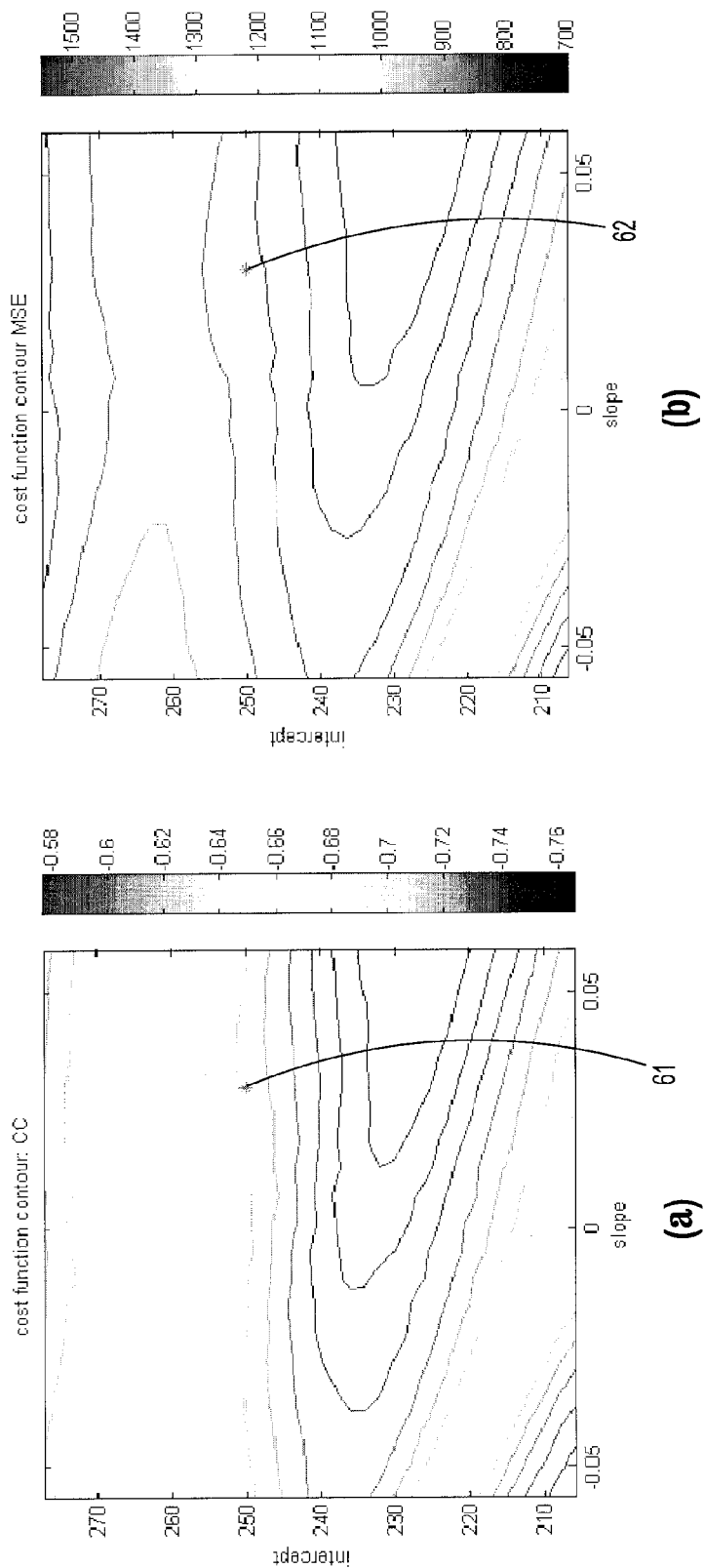
FIGS. 6(a)-(b) show cost function contours for the CC and MSE similarity measures, according to an embodiment of the invention.
Figure 7:
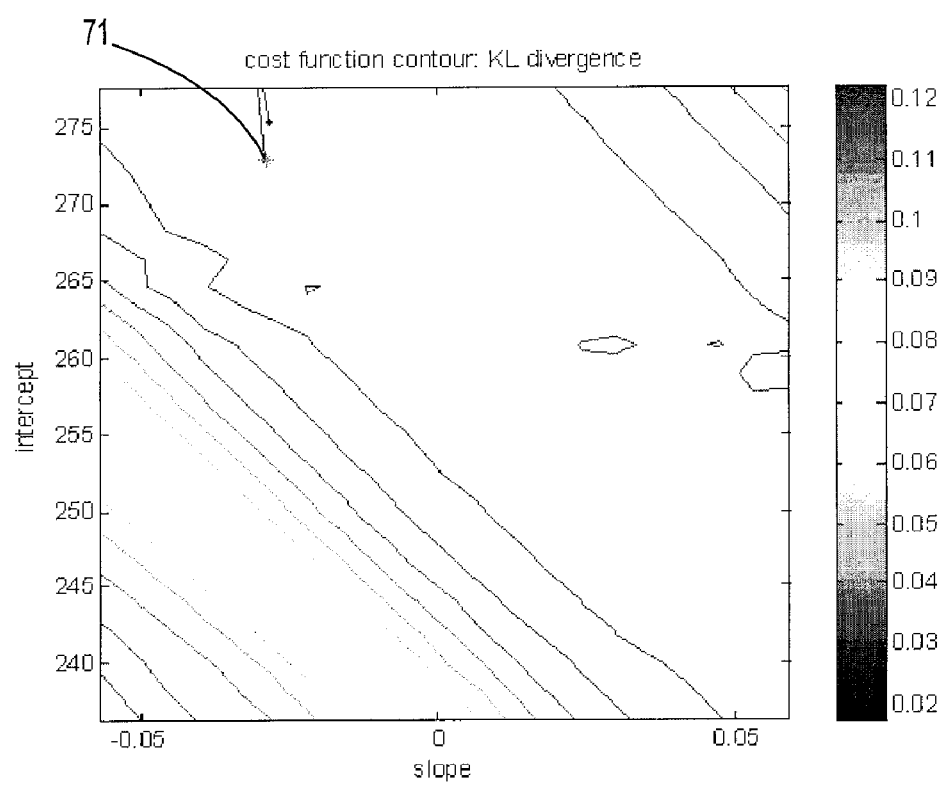
FIG. 7 shows a cost function contour for the KLD similarity measure, according to an embodiment of the invention.
Figure 8:
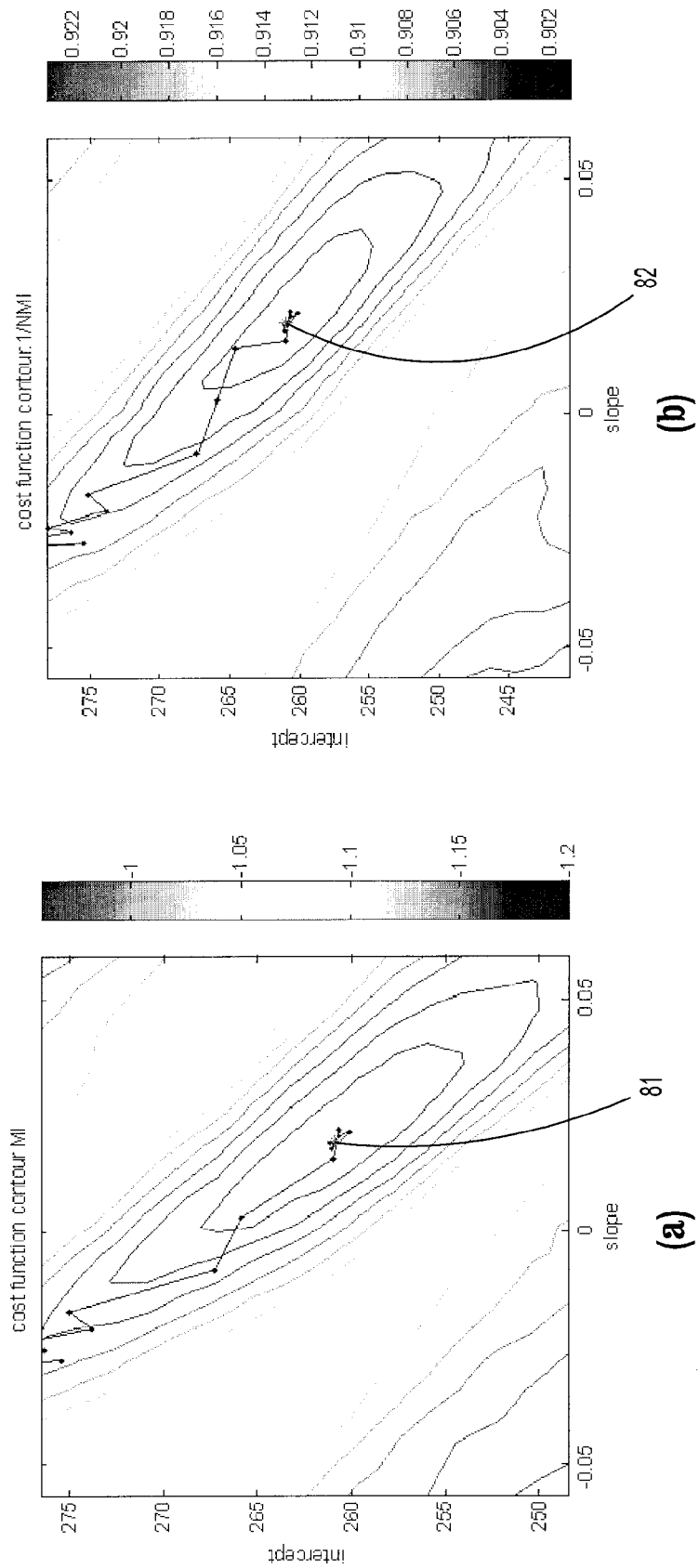
FIGS. 8(a)-(b) shows a cost function contour for the MI and NMI similarity measures, according to an embodiment of the invention.
Figure 9:
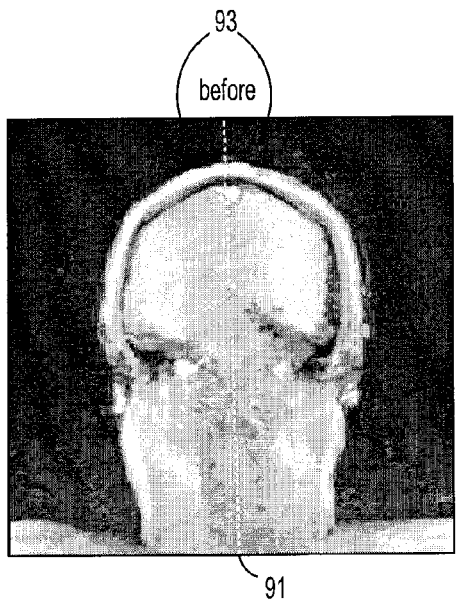
FIGS. 9(a)-(b) illustrate consistency tuning using the KL divergence, according to an embodiment of the invention.
Figure 9:
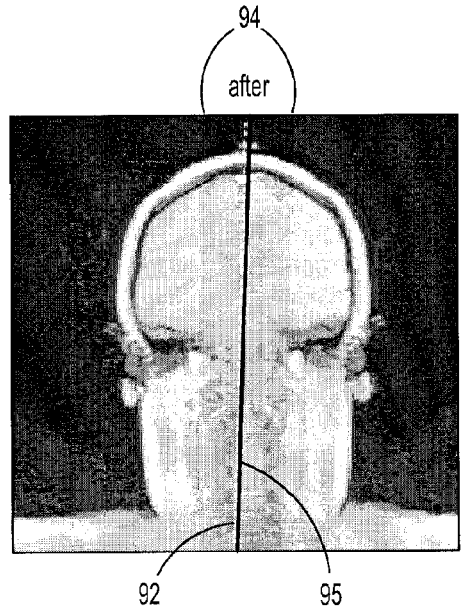
Figure 10:
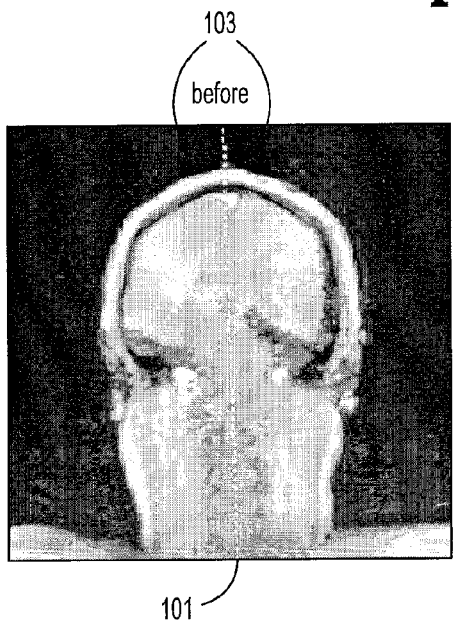
FIGS. 10(a)-(b) illustrate consistency tuning using the MI, according to an embodiment of the invention.
Figure 10:
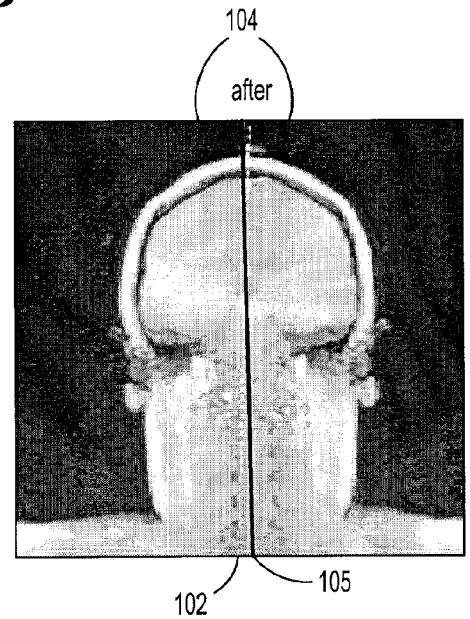
Figure 11:
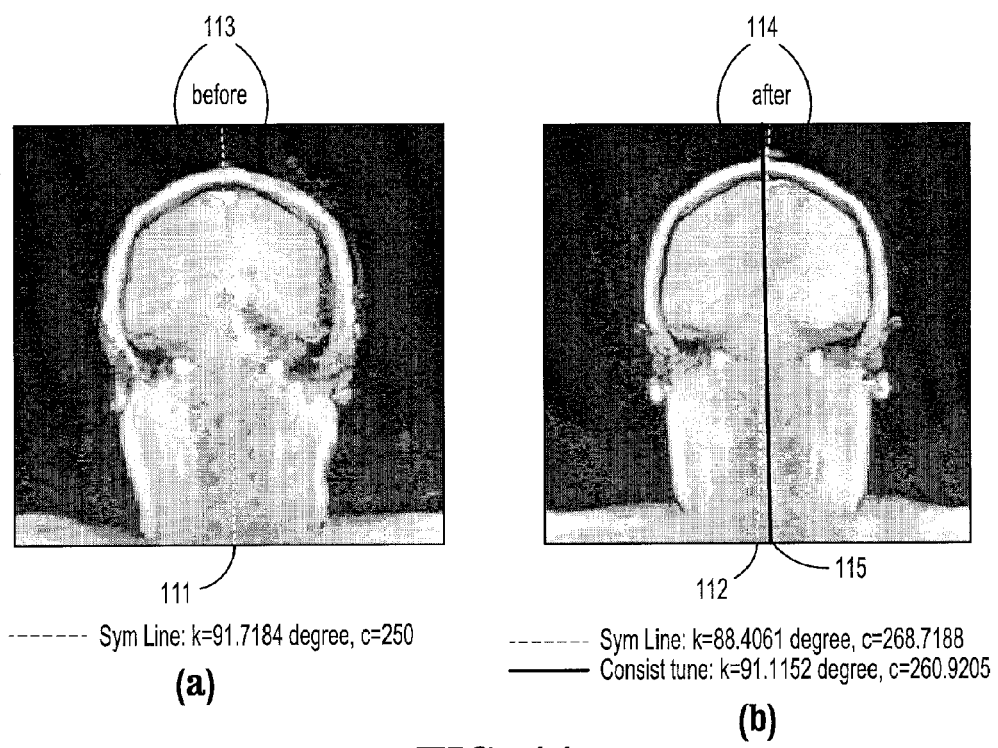
FIGS. 11(a)-(b) illustrate consistency tuning by using the NMI, according to an embodiment of the invention.

Cost function contours for the CC, MSE, KLD, MI, and NMI similarity measures are shown in FIGS. 6(a) and (b), 7, and 8(a) and (b), respectively. In each contour plot, the crosses 61, 62, 71, 81, and 82 mark the intercept and slope for the reference study.

It can be seen from the contours that the CC and MSE cost functions cannot provide a local minimum for the algorithm to search. The KL divergence provides a very flat searching plane, which is difficult for the search to adapt to. Both MI and NMI provide a clear minimum for the search. FIGS. 9(a)-(b), 10(a)-(b), and 11(a)-(b) illustrate consistency tuning using KLD, MI, and NMI, respectively, according to an embodiment of the invention. In each case, the (a) sub-figure is the reference image, and the (b) sub-figure is the composed image after consistency tuning. In the figures, reference numbers 91, 101, and 111 refer to the middle line of the reference image, reference numbers 92, 102, and 112 refer to the middle line of the composed image before consistency tuning, reference numbers 93, 94, 103, 104, 113, and 114 are the respective tuning ranges, and 95, 105, and 115 are the lines after consistency tuning. Slopes and intercepts for each of the lines are provided in the captions below the figures. The consistency tuning using KLD provides poor results, while the results from using MI and NMI are both good. However, NMI provides a less sensitive search due to a small gradient between the contour line. Therefore, MI is used as a similarity measure in a 3D consistency tuning study according to an embodiment of the invention.

Similarity Measure within the Object of Interest

Figure 12:
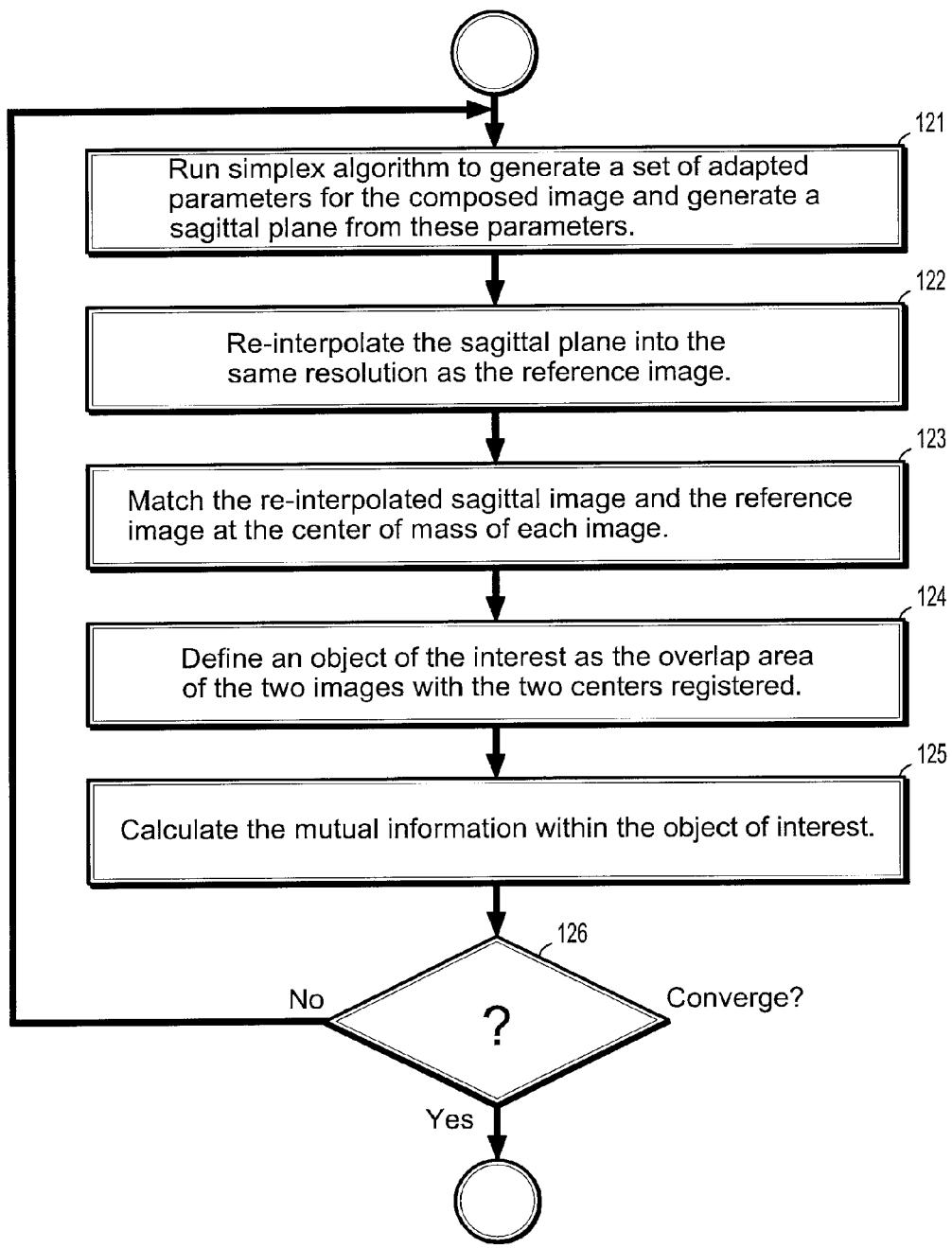
FIG. 12 is a flowchart of a consistency tuning method according to an embodiment of the invention.
Figure 13:
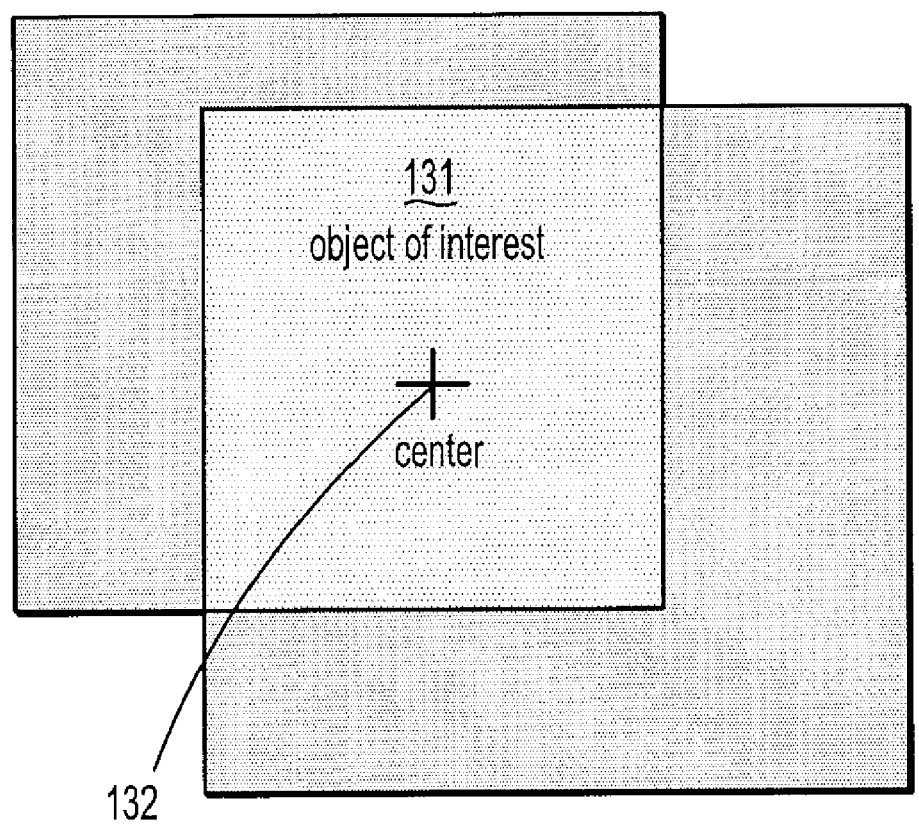
FIG. 13 illustrates the definition of an object of interest, according to an embodiment of the invention.

In 2D images, the similarity is calculated within a tuning range along the middle line. For the 3D images, the similarity is calculated between the interpolated sagittal plane generated from the adapted parameters ($k_1$, $c_1$, $k_2$, $c_2$) and the reference sagittal plane. The resolution and the head locations in the images from the different scans can be quite different, and the MI is sensitive to image gray level matched on the same position. FIG. 12 is a flowchart of a method for consistency tuning method according to an embodiment of the invention, as calculated from the similarity measure for the 3D images. Referring now to the figure, first, at step 121, an optimization algorithm, such as the simplex algorithm, is run to generate a set of adapted parameters ($k_1, c_1, k_2, c_2$) for the scan chosen as the composed image that maximizes the similarity function, and a sagittal plane is generated from these parameters. At step 122, the sagittal plane is re-interpolated into the same resolution as the reference image. At step 123, the re-interpolated sagittal image and the reference image are matched at the center of mass of each image, as based on the image intensities. At step 124, define an object of the interest as the overlap area 131 of the two images with the two centers 132 registered, as shown in FIG. 13. At step 125, the mutual information is then calculated within the object of interest. At step 126, the mutual information is compared with a previous value for convergence, and steps 121 to 125 are repeated until the mutual information similarity measure converges to a maximum value.

Results: Algorithm Validation—Self Reference

A consistency tuning algorithm according to an embodiment of the invention assumes that the sagittal images of both scans are as similar as possible. In real data, the gray level histogram, the head position, and the image resolution can all affect this assumption. One of way to validate if the consistency tuning algorithm works is to use self reference tuning. To do this, first, manually set the parameters ($k_1, c_1, k_2, c_2$) to generate a reference image, where $k_1, c_1$, are the slope and intercepts of the transverse localizer image, and $k_2, c_2$ are the slope and intercepts of the coronal localizer image, and then implement consistency tuning to determine if the sagittal image after tuning is as similar as the reference image. There are at least three ways of checking to validate the consistency tuning: (1) visually inspect the tuning image and the reference image; (2) check if the convergence MI close to the MI between reference image itself; and (3) check if the convergence values for $k_1, k_2$ are close to the manually set values, and the sum of the convergence intercept value $c_1+c_2$ is close to the manually set value. For this validation, images the first study were used.

The parameter values were manually changed in 3 ways.

(1) Change only the intercepts $c_1$ and $c_2$. The results are as follows.

|  | $k_1$ | $c_1$ | $k_2$ | $c_2$ |
| --- | --- | --- | --- | --- |
| Compose study | 0.00849 | 87.094 | 0.01693 | 86.4427 |
| Reference study | 0.00849 | 92.094 | 0.01693 | 91.4427 |
| Converged values | 0.00849 | 95.01 | 0.01693 | 88.53 |

Figure 14:
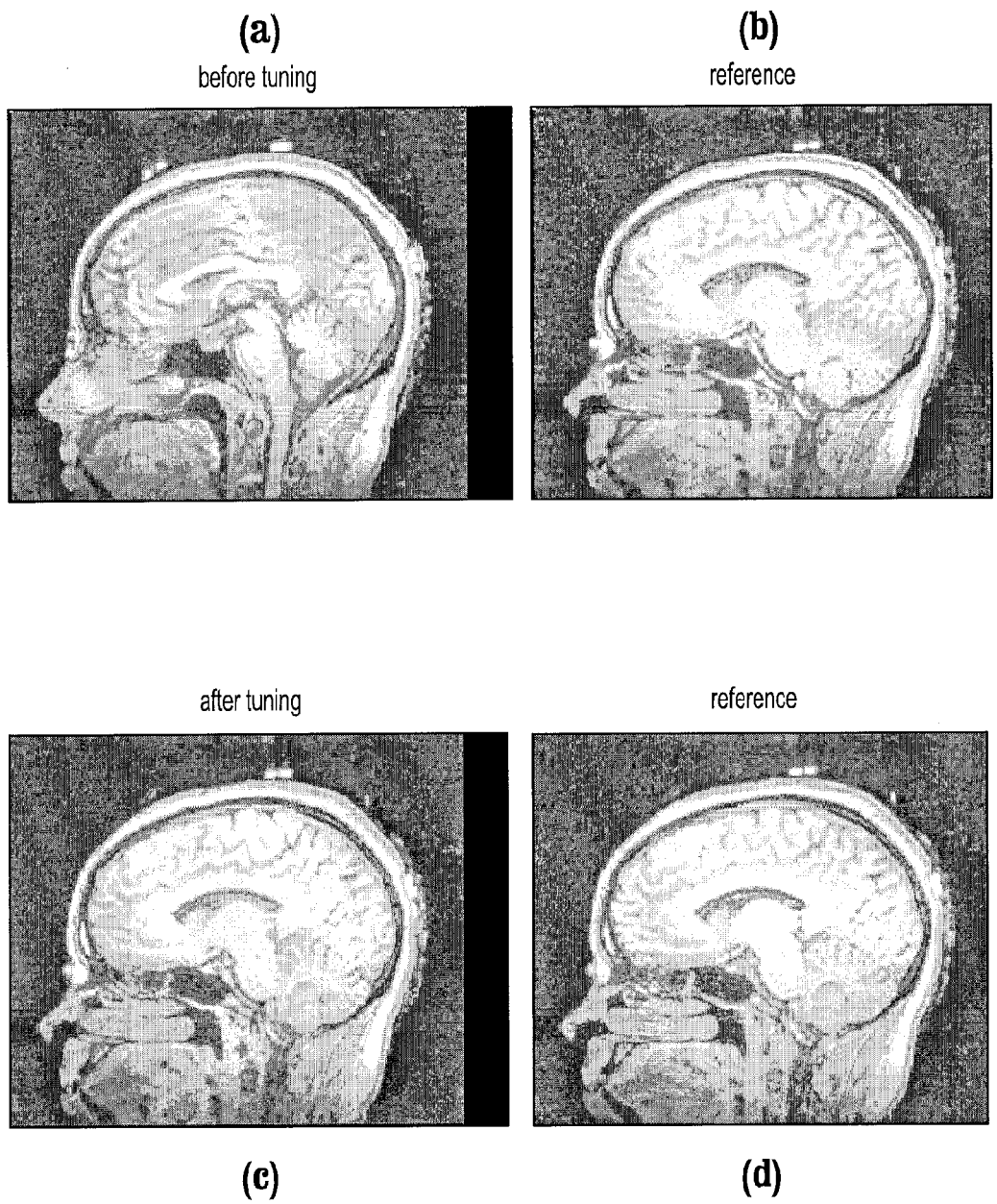
FIGS. 14(a)-(d) illustrate consistency tuning results of a self reference test involving only the intercepts, according to an embodiment of the invention.

Before tuning, the mutual information between the composed image and the reference image is 1.3086. The mutual information between the reference image and the reference image is 6.1773. After consistency tuning, the mutual information between the composed image and the reference image is 6.168, which is very close to 6.1773. The converged slopes are the same as the manually set slopes. The intercepts sum, 183.54, is the same as the manually set sum, 183.54. By visual inspection, one can also see that after tuning, the image is very close to the reference. FIGS. 14(*a*)-(*d*) show the consistency tuning results, with FIGS. 14(*a*) and (*c*) being the before and after, respectively, for the composed image, and FIGS. 14(*b*) and (*d*) being the reference image.

(2) Change only the slopes $k_1$ and $k_2$. The results are as follows.

|  | $k_1$ | $c_1$ | $k_2$ | $c_2$ |
| --- | --- | --- | --- | --- |
| Compose study | 0.00849 | 87.094 | 0.01693 | 86.4427 |
| Reference study | 0.03 | 87.094 | 0.05 | 86.4427 |
| Converged values | 0.03 | 85.14 | 0.05 | 88.40 |

Figure 15:
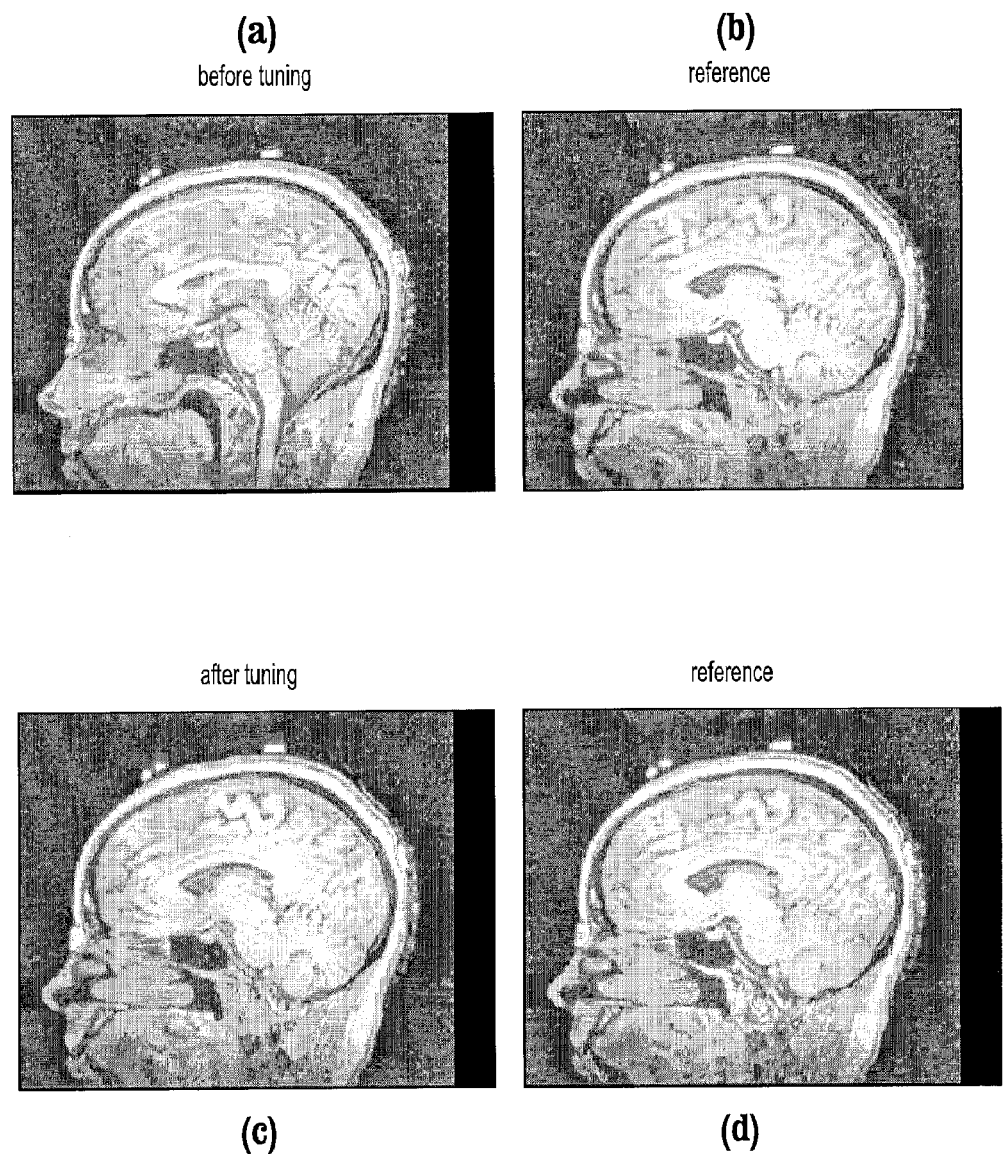
FIGS. 15(a)-(d) illustrate consistency tuning results of a self reference test involving only slopes, according to an embodiment of the invention.

Before tuning, the mutual information between the composed image and the reference image is 1.4242. The mutual information between the reference image and the reference image is 6.0612. After consistency tuning, the mutual information between the composed image and the reference image is 6.032, which is close to 6.0612. The converged slope is the same as the manually set slope. The intercepts sum, 173.54, is the same as the manually set sum, 173.54. By visual inspection, one also see that after tuning, the image is very close to the reference. FIGS. 15(*a*)-(*d*) show the consistency tuning results, with FIGS. 15(*a*) and (*c*) being the before and after, respectively, for the composed image, and FIGS. 15(*b*) and (*d*) being the reference image.

(3) Change both the slopes $k_1, k_2$ and the intercepts $c_1, c_2$. The results are as follows.

|  | $k_1$ | $c_1$ | $k_2$ | $c_2$ |
| --- | --- | --- | --- | --- |
| Compose study | 0.00849 | 87.094 | 0.01693 | 86.4427 |
| Reference study | 0.03 | 92.094 | 0.05 | 91.4427 |
| Converged values | 0.03 | 91.81 | 0.05 | 91.73 |

Figure 16:
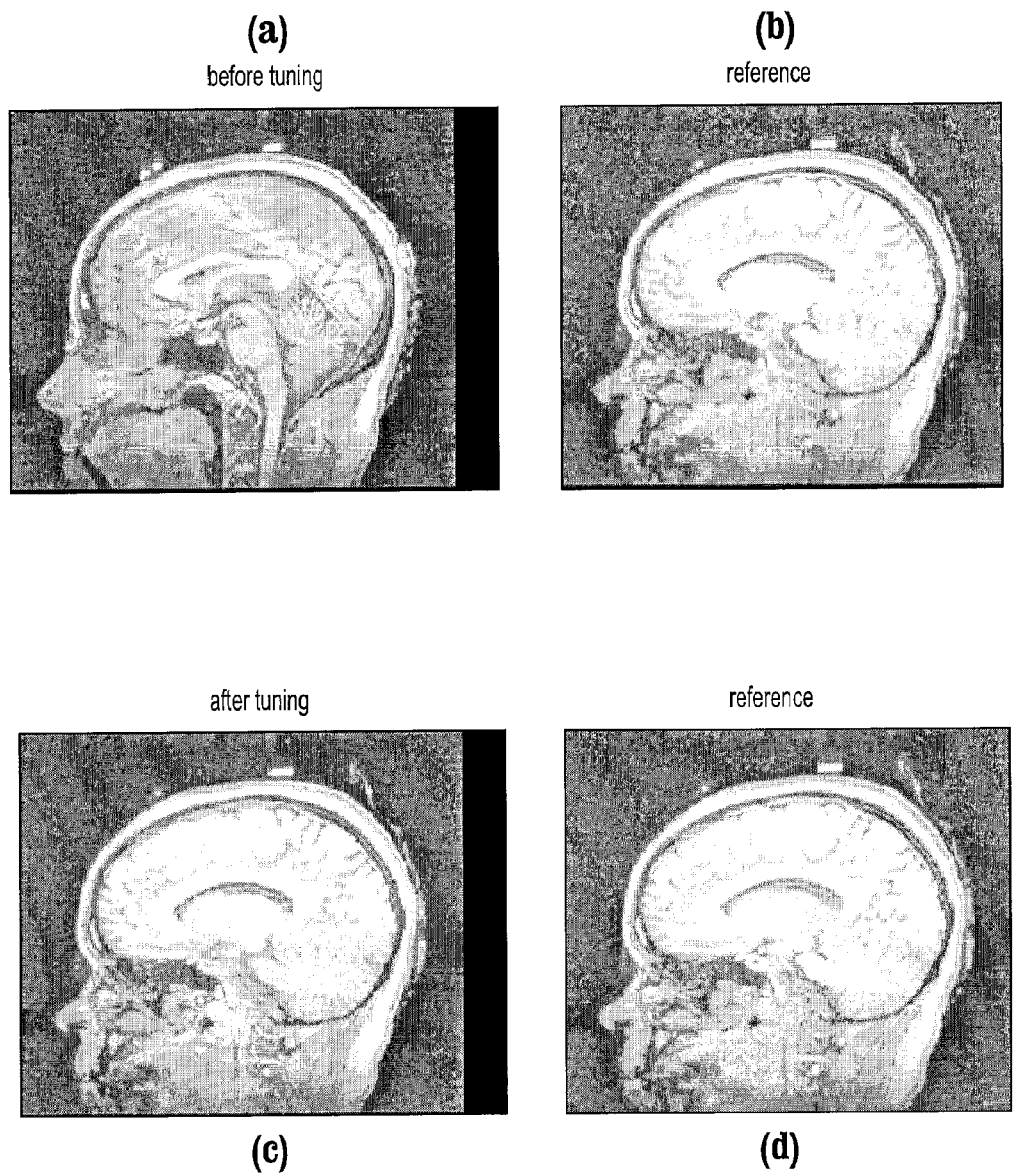
FIGS. 16(a)-(d) illustrate consistency tuning results of a self reference test using both intercepts and slopes, according to an embodiment of the invention.

Before tuning, the mutual information between the composed image and the reference image is 1.2215. The mutual information between the reference image and the reference image is 6.4860. After consistency tuning, the mutual information between the composed image and the reference image is 6.462, which is close to 6.4860. The converged slope is very close to the manually set slope. The intercepts sum, 183.54, is the same as the manually set sum, 183.54. By visual inspection, one can also see that after tuning, the image is very close to the reference. FIGS. 16(*a*)-(*d*) show the consistency tuning results, with FIGS. 16(*a*) and (*c*) being the before and after, respectively, for the composed image, and FIGS. 16(*b*) and (*d*) being the reference image.

Results: Consistency Tuning Between Different Scans

Figure 17:
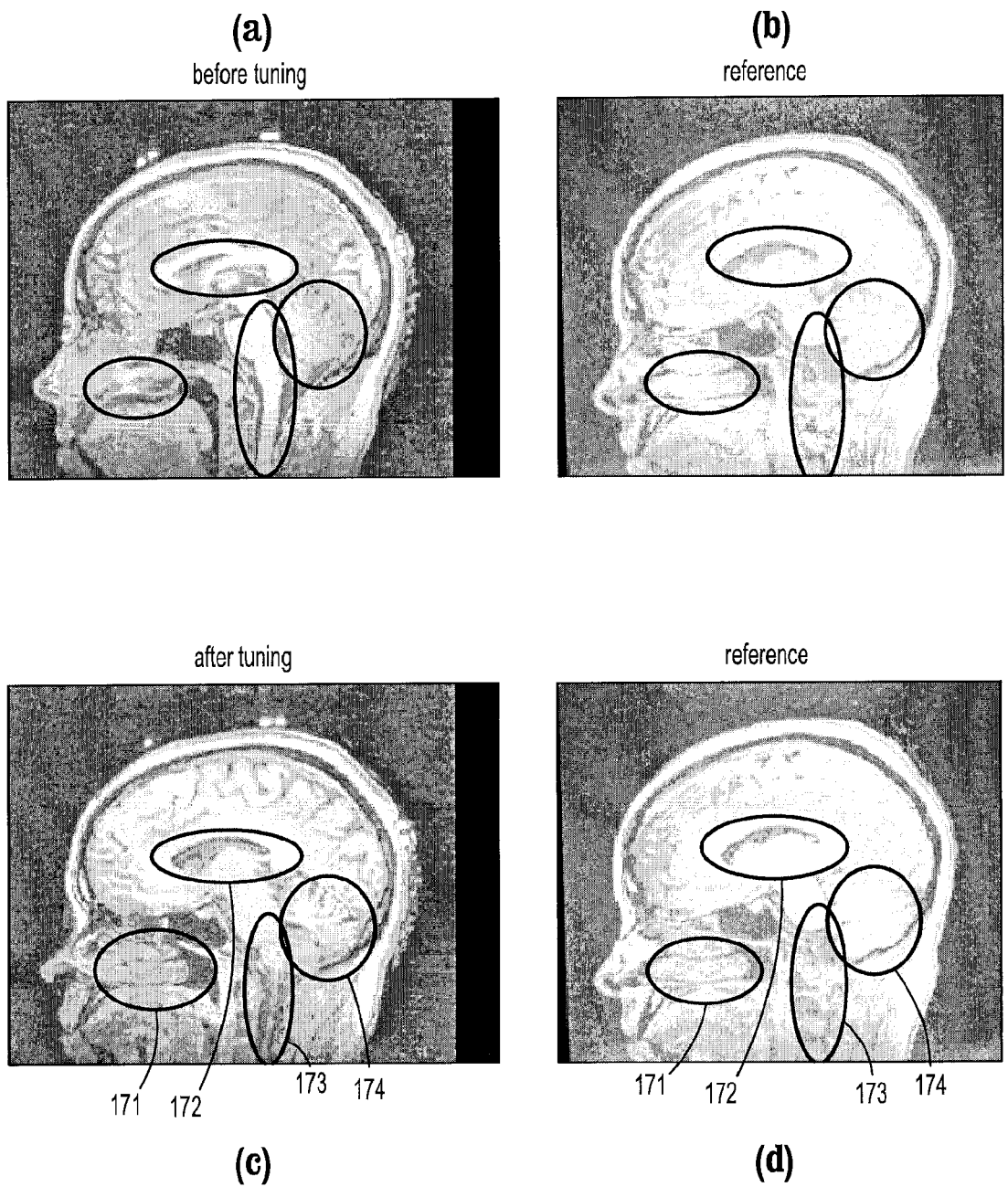
FIGS. 17(a)-(d) shows the consistency tuning results between different scans, according to an embodiment of the invention.

For consistency tuning between different scans, the scan images can be taken at different position and using different resolutions. Although the converged slope and the sum of the intercepts cannot be directly compared, the tuned image can be checked by visual inspection. Here is shown an example between different scans of the patient, with compose study image and a reference study image. FIGS. 17(*a*)-(*d*) show the consistency tuning results, with FIGS. 17(*a*) and (*c*) being the before and after, respectively, for the composed image, and FIGS. 17(*b*) and (*d*) being the reference image. By visual inspection, one can see that after tuning, the image is close to the reference. Differences between composed image before and after tuning, as compared to the reference images, are indicated by circles regions 171, 172, 173, 174. For clarity, the circled regions are only indicated for the (c) and (d) figures.

System Implementations

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 18:
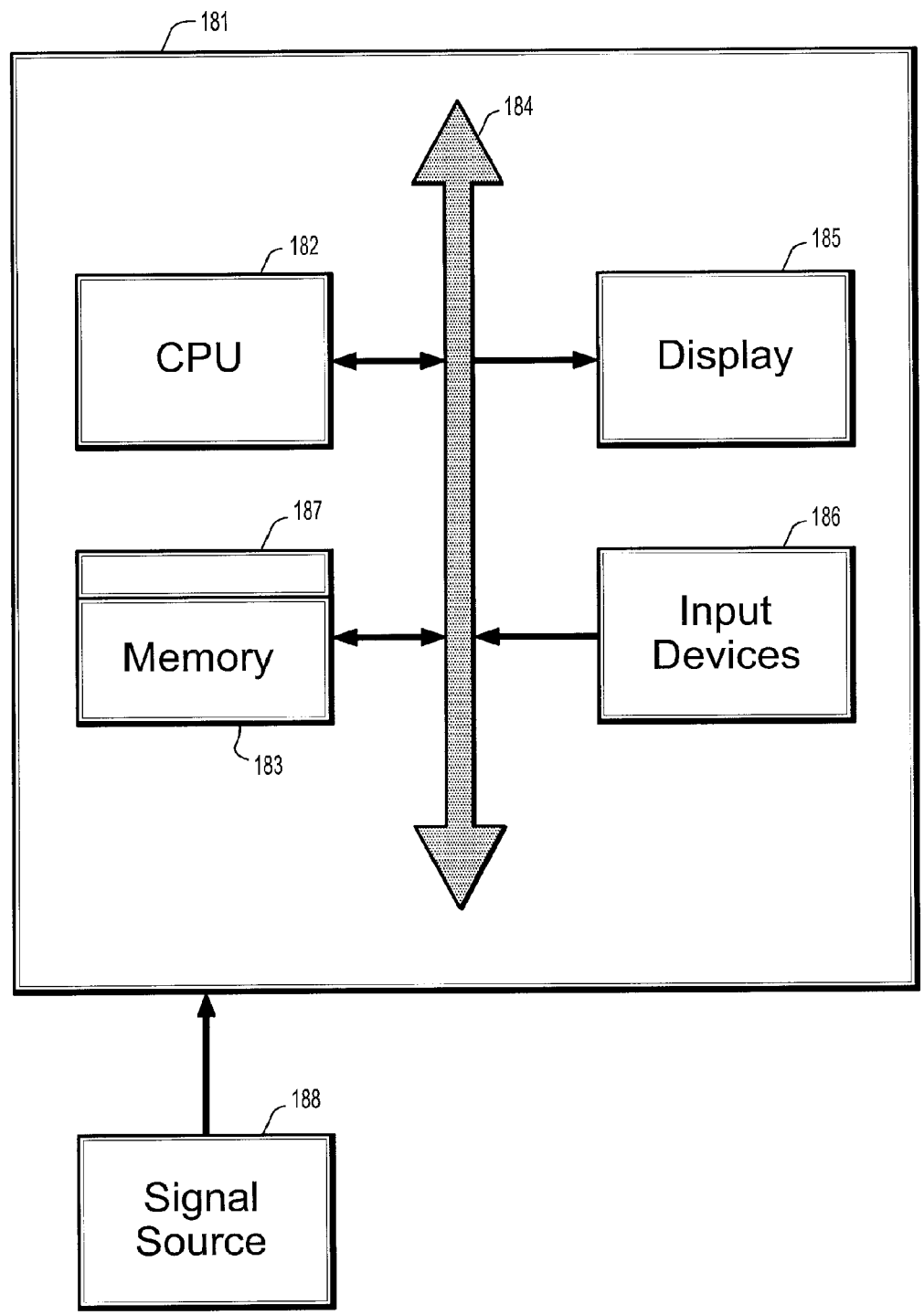
FIG. 18 is a block diagram of an exemplary computer system for implementing a method for the detection of mid-sagittal planes in magnetic resonance (MR) images, according to an embodiment of the invention.

FIG. 18 is a block diagram of an exemplary computer system for implementing a method for the detection of mid-sagittal planes in magnetic resonance (MR) images, according to an embodiment of the invention. Referring now to FIG. 18, a computer system 181 for implementing the present invention can comprise, inter alia, a central processing unit (CPU) 182, a memory 183 and an input/output (I/O) interface 184. The computer system 181 is generally coupled through the I/O interface 184 to a display 185 and various input devices 186 such as a mouse and a keyboard. The support circuits can include circuits such as cache, power supplies, clock circuits, and a communication bus. The memory 183 can include random access memory (RAM), read only memory (ROM), disk drive, tape drive, etc., or a combinations thereof. The present invention can be implemented as a routine 187 that is stored in memory 183 and executed by the CPU 182 to process the signal from the signal source 188. As such, the computer system 181 is a general purpose computer system that becomes a specific purpose computer system when executing the routine 187 of the present invention.

The computer system 181 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method of finding consistent mid-sagittal planes (MSPs) in different image head scans of a same patient, said method comprising the steps of:
providing a pair of images acquired from different head scans of a same patient, each said image comprising a plurality of intensities associated with a 3-dimensional (3D) grid of points;
for each image,
selecting a 2-dimensional (2D) transverse localizer image from a middle slice along a transverse view of the 3D image;
fitting an ellipse to said transverse localizer image to locate a head position (x, y) in said transverse localizer image, wherein said y-coordinate, a position along a vertical axis, is indicative of a position of a 2D coronal localizer image in the 3D image;
fitting an ellipse to said coronal localizer image to locate a head position (x, y) in said coronal localizer image, wherein said x-coordinate, a position along a horizontal axis, is indicative of a position of said 2D coronal localizer image in the 3D image;
calculating a middle line in said transverse localizer image and a middle line in said coronal localizer image;
calculating a mid-sagittal plane (MSP) from the middle lines of said transverse localizer image and said coronal localizer image; and
determining a new set of slope and intercept parameters within a proximity of one MSP that maximizes a similarity measure between the one MSP and the other MSP.

2. The method of claim 1, wherein if the middle lines of said transverse localizer image and said coronal localizer image intersect each other, calculating said mid-sagittal plane from the plane defined by the intersection of said middle lines.

3. The method of claim 1, wherein if the middle lines of said transverse localizer image and said coronal localizer image do not intersect each other, calculating said mid-sagittal plane further comprises finding points $p_1$, $p_2$ on each respective middle lines that are closest to each other, finding a mid-pint $p_m$ on a line segment connecting points $p_1$, $p_2$, and defining said MSP as a plane passing through point $p_m$ that whose normal is determined by a cross product of vectors corresponding to said middle lines.

4. The method of claim 1, further comprising, for each 3D image, updating a column resolution and row resolution of said corresponding MSP with information from each selected transverse and coronal localizer image.

5. The method of claim 1, wherein said slope and intercept parameters are the slope and intercept of the middle lines of the transverse localizer image and the coronal localizer image associated with the MSP.

6. The method of claim 1, wherein said similarity measure is a mutual information measure proportional to $$-\sum_x \sum_y p(x, y) \log\left(\frac{p(x, y)}{p(x)p(y)}\right),$$

wherein x, y represent respectively intensity levels of corresponding points in each of the two MSPs, p(x) is a probability of intensity level x, and p(x, y) is a joint probability of intensity levels x, y.

7. The method of claim 1, wherein said similarity measure is maximized using a simplex algorithm.

8. The method of claim 1, further comprising:
generating a new sagittal plane for the one 3D image from said new set of slope and intercept parameters;
re-interpolating said new sagittal plane into a same resolution as the MSP of the other 3D image;
matching the re-interpolated sagittal plane and the other MSP at a center of mass point of each sagittal image;
defining an object of interest as an overlap area of the two sagittal images with the center of mass points registered; and
calculating said similarity measure over said object of interest.

9. The method of claim 8, further comprising repeating the steps of claim 8 until said similarity measure converges to a maximum value.

10. A method of finding consistent mid-sagittal planes (MSPs) in different image head scans of a same patient, said method comprising the steps of:

providing a pair of images acquired from different head scans of a same patient, each said image comprising a plurality of intensities associated with a 3-dimensional (3D) grid of points;

for each image, selecting a 2-dimensional (2D) transverse localizer image from a middle slice along a transverse view of the 3D image, and finding a 2D coronal localizer image in said 3D image, and calculating a mid-sagittal plane from the middle lines of said transverse localizer image and said coronal localizer image;

re-interpolating the MSP of one 3D image into a same resolution as the MSP of the other 3D image;

matching the re-interpolated MSP and the other MSP at a center of mass point of each sagittal image;

defining an object of interest as an overlap area of the two sagittal images with the center of mass points registered;

maximizing a similarity measure over said object of interest to generate a set of slope and intercept parameters of middle lines of the transverse localizer image and the coronal localizer image associated with the one MSP that makes the one MSP consistent with the other MSP.

11. The method of claim 10, further comprising, for each 3D image:

fitting an ellipse to said transverse localizer image to locate a head position (x, y) in said transverse localizer image, wherein said y-coordinate. A position along a vertical axis, is indicative of a position of said 2D coronal localizer image in the 3D image;

fitting an ellipse to said coronal localizer image to locate a head position (x, y) in said coronal localizer image, wherein said x-coordinate, a position along a horizontal axis, is indicative of a position of said 2D coronal localizer image in the 3D image;

calculating said middle lines in said transverse localizer image and said coronal localizer image; and calculating said mid-sagittal plane from the middle lines of said transverse localizer image and said coronal localizer image.

12. The method of claim 10, further comprising repeating the steps of re-interpolating the one MSP into the resolution of the other MSP, matching the re-interpolated MSP and the other MSP, defining an object of interest, and maximizing a similarity measure over said object of interest until said similarity measure converges to a maximum value.

13. A program storage device readable by a computer, tangibly embodying a program of instructions executable by the computer to perform the method steps for finding consistent mid-sagittal planes (MSPs) in different image head scans of a same patient, said method comprising the steps of:

providing a pair of images acquired from different head scans of a same patient, each said image comprising a plurality of intensities associated with a 3-dimensional (3D) grid of points;

for each image, selecting a 2-dimensional (2D) transverse localizer image from a middle slice along a transverse view of the 3D image;

fitting an ellipse to said transverse localizer image to locate a head position (x, y) in said transverse localizer image, wherein said y-coordinate, a position along a vertical axis, is indicative of a position of a 2D coronal localizer image in the 3D image;

fitting an ellipse to said coronal localizer image to locate a head position (x, y) in said coronal localizer image, wherein said x-coordinate, a position along a horizontal axis, is indicative of a position of said 2D coronal localizer image in the 3D image;

calculating a middle line in said transverse localizer image and a middle line in said coronal localizer image;

calculating a mid-sagittal plane (MSP) from the middle lines of said transverse localizer image and said coronal localizer image; and determining a new set of slope and intercept parameters within a proximity of one MSP that maximizes a similarity measure between the one MSP and the other MSP.

14. The computer readable program storage device of claim 13, wherein if the middle lines of said transverse localizer image and said coronal localizer image intersect each other, calculating said mid-sagittal plane from the plane defined by the intersection of said middle lines.

15. The computer readable program storage device of claim 13, wherein if the middle lines of said transverse localizer image and said coronal localizer image do not intersect each other, calculating said mid-sagittal plane further comprises finding points $p_1$, $p_2$ on each respective middle lines that are closest to each other, finding a mid-pint $p_m$ on a line segment connecting points $p_1$, $p_2$, and defining said MSP as a plane passing through point $p_m$ that whose normal is determined by a cross product of vectors corresponding to said middle lines.

16. The computer readable program storage device of claim 13, the method further comprising, for each 3D image, updating a column resolution and row resolution of said corresponding MSP with information from each selected transverse and coronal localizer image.

17. The computer readable program storage device of claim 13, wherein said slope and intercept parameters are the slope and intercept of the middle lines of the transverse localizer image and the coronal localizer image associated with the MSP.

18. The computer readable program storage device of claim 13, wherein said similarity measure is a mutual information measure proportional to $$-\sum_x \sum_y p(x, y) \log\left(\frac{p(x, y)}{p(x)p(y)}\right),$$

wherein x, y represent respectively intensity levels of corresponding points in each of the two MSPs, p(x) is a probability of intensity level x, and p(x, y) is a joint probability of intensity levels x, y.

19. The computer readable program storage device of claim 13, wherein said similarity measure is maximized using a simplex algorithm.

20. The computer readable program storage device of claim 13, the method further comprising:

generating a new sagittal plane for the one 3D image from said new set of slope and intercept parameters;

re-interpolating said new sagittal plane into a same resolution as the MSP of the other 3D image;

matching the re-interpolated sagittal plane and the other MSP at a center of mass point of each sagittal image;

defining an object of interest as an overlap area of the two sagittal images with the center of mass points registered; and calculating said similarity measure over said object of interest.

21. The computer readable program storage device of claim 20, the method further comprising repeating the steps of claim 20 until said similarity measure converges to a maximum value.

* * * * *